United States Patent [19]

Kangouri et al.

[11] 4,197,292
[45] Apr. 8, 1980

[54] NOVEL AMYLASE INHIBITORS

[75] Inventors: Kunio Kangouri, Kitamoto; Shinjuro Namiki, Omiya; Takatoshi Nagate, Kashiwa; Kazuhiko Sugita, Omiya; Sadafumi Omura, Ageo, all of Japan

[73] Assignee: Taisho Pharmaceutical Co., Tokyo, Japan

[21] Appl. No.: 9,157

[22] Filed: Feb. 2, 1979

[30] Foreign Application Priority Data

Feb. 10, 1978 [JP] Japan ................................ 53-14407
Feb. 10, 1978 [JP] Japan ................................ 53-14408

[51] Int. Cl.$^2$ ............................................ A61K 35/00
[52] U.S. Cl. ................................. 424/116; 435/169
[58] Field of Search ..................... 424/116; 195/80 R; 435/169

[56] References Cited

U.S. PATENT DOCUMENTS 4,010,258  3/1977  Murao ................................... 424/115
4,062,950  12/1977  Frommer et al. .................... 424/181

FOREIGN PATENT DOCUMENTS 52-24119  6/1977  Japan .

OTHER PUBLICATIONS

Niwa et al., Agr. Biol. Chem., 34, 966-968 (1970).

Primary Examiner—Jerome D. Goldberg
Attorney, Agent, or Firm—George A. Loud

[57] ABSTRACT

Novel oligosaccharide substances, TAI-A and TAI-B, possessing a strong inhibitory activity to amylase and invertase are obtained by inoculating a seed of the strain of Streptomyces calvus TM-521 into aqueous nutrient medium, cultivating this with shaking or by a submerged culture method with aeration, and separating the produced amylase inhibitors TAI-A and TAI-B from the cultured broth.

2 Claims, 6 Drawing Figures

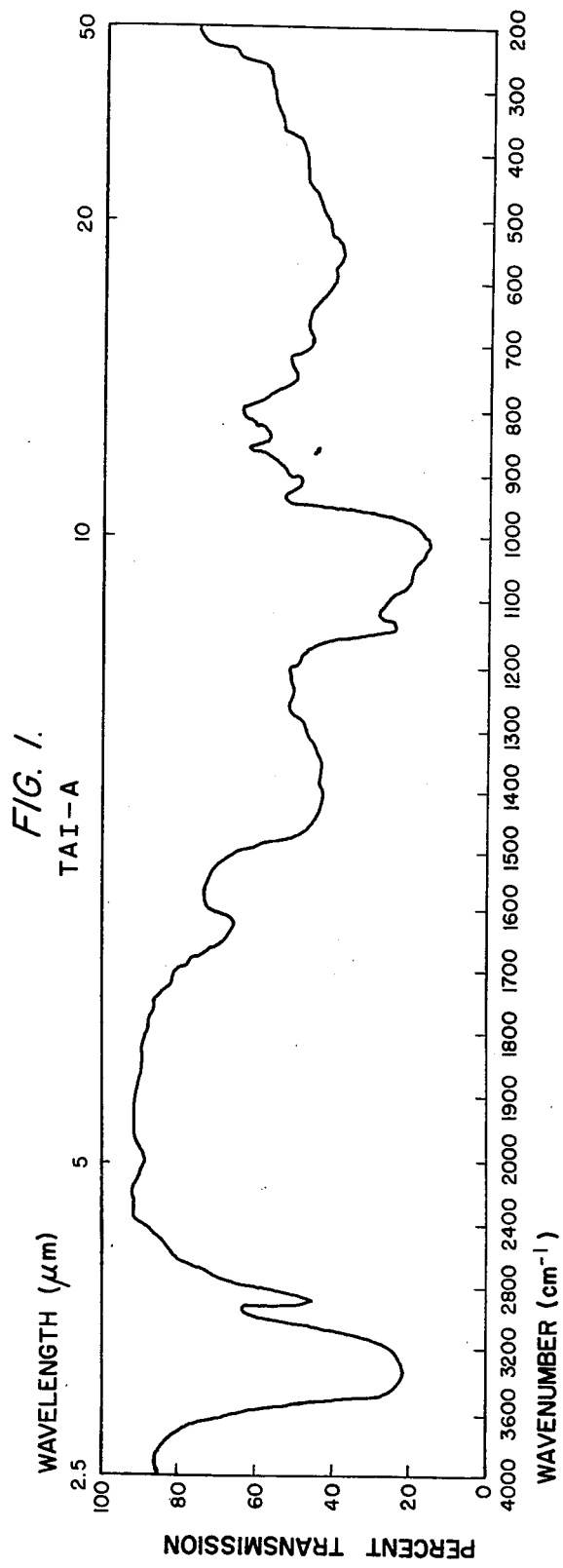
FIG. 1. TAI-A
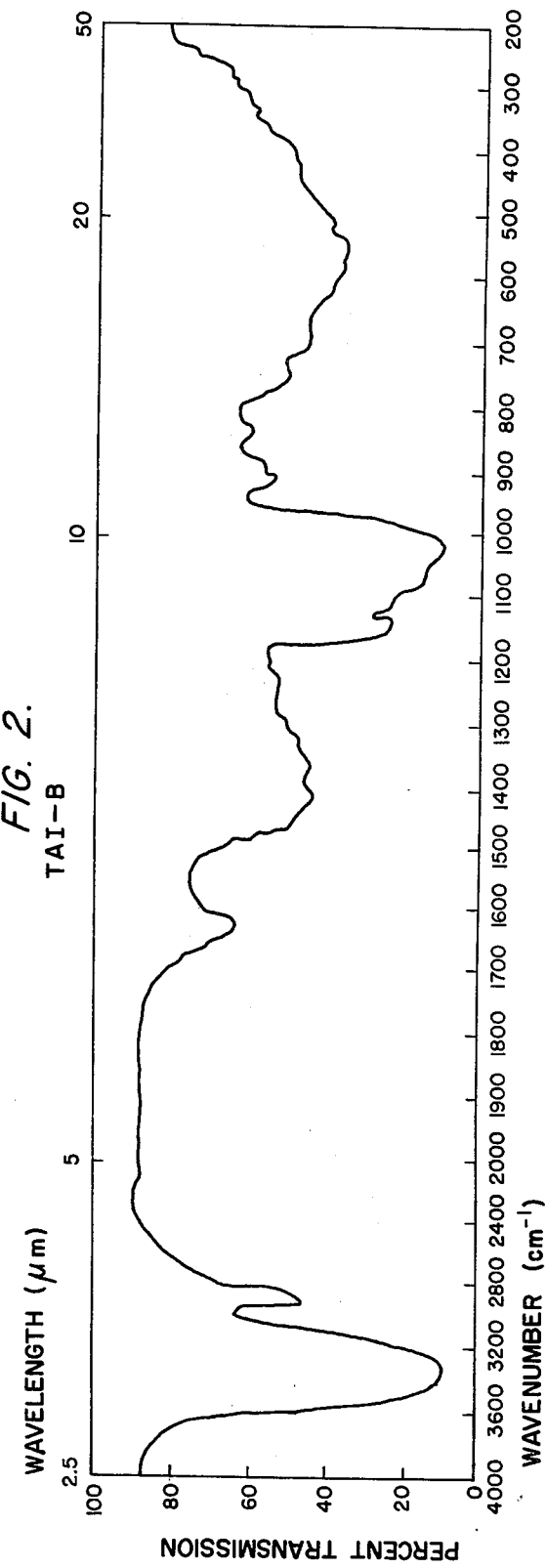
FIG. 2. TAI-B

TAI-A

TAI-B

NOVEL AMYLASE INHIBITORS

BACKGROUND OF THE INVENTION

Prior art oligosaccharide-like amylase inhibitors, Nojirimycin [Agr. Biol. Chem., 34, 966(1970)], S-AI(Amylostatin) [U.S. Pat. No. 4,010,258], NCGAI [Japanese Pat. Laying-Open No. 54,990/76, Japanese Patent Publication No. 24119/77], and the aminosugar derivatives by Frommer et al [U.S. Pat. No. 4,062,950].

The novel oligosaccharide-like amylase inhibitors of this invention, TAI-A and TAI-B, are distinguished from Nojirimycin in terms of lack of their inhibitory activity to α-glucosidase, from S-AI in terms of their adsorption to acidic and basic ion exchange resins and lack of their inhibitory activity to bacterial liquefying α-amylase, from NCGAI in terms of their optical activity and lack of their inhibitory activity to bacterial liquefying α-amylase, and from the aminosugar derivatives of Frommer et al in terms of lack of methyl groups in their molecules.

BRIEF SUMMARY OF THE INVENTION

This invention relates to new amylase inhibitors and to processes for their production. More particularly, this invention is concerned with novel amylase inhibitors designated as TAI-A and TAI-B, which are derived from a new strain of the microorganism belonging to Streptomyces calvus, and with the processes for the preparation of said inhibitors.

The purpose of this invention is to provide microbial products possessing the inhibitory activity to amylase and invertase. It is still another purpose of this invention to provide processes for preparing the amylase inhibitors, TAI-A and TAI-B.

TAI-A and TAI-B of this invention may be produced by cultivation of a newly isolated microbial strain of Streptomyces calvus, and each of them is obtained as amorphous powders according to the processes of this invention. Both TAI-A and TAI-B belong to the oligosaccharide group amylase inhibitors, and are useful for combating obesity, diabetes, prediabetes, gastritis, gastric ulcer, hyperglycemia, hyperlipemia and the like.

The microbial strain, which produces TAI-A and TAI-B, was isolated from a soil sample and was designated by the applicants as Streptomyces calvus TM-521 (ATCC No. 31,478).

BRIEF DESCRIPTION OF THE DRAWINGS

FIG. 1 shows the infrared absorption spectrum of TAI-A using a tablet of KBr.

FIG. 2 shows the infrared absorption spectrum of TAI-B using a tablet of KBr.

DETAILED DESCRIPTION OF THE INVENTION

Figure 3:
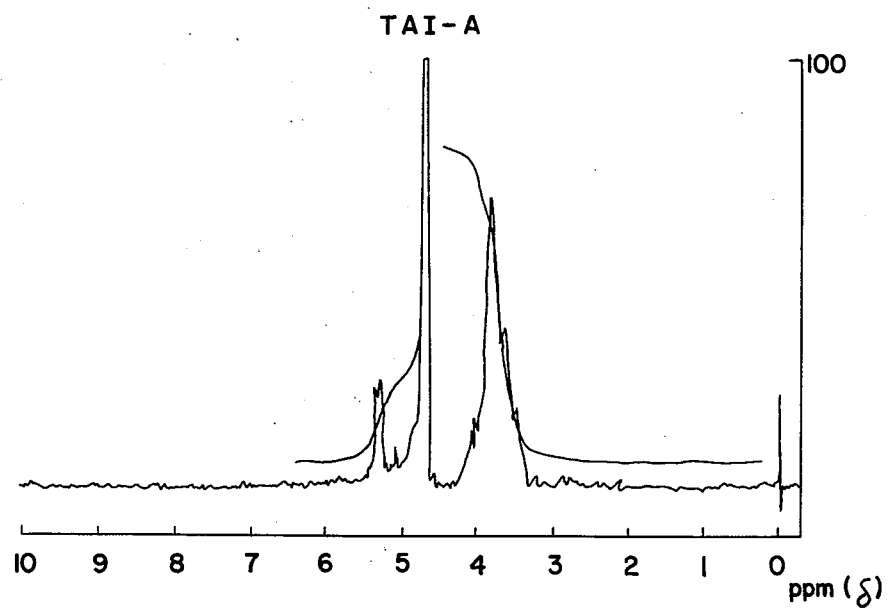
FIG. 3 shows the nuclear magnetic resonance spectrum of TAI-A in $D_2O$.

The new amylase inhibitors, TAI-A and TAI-B, may be prepared by the cultivation under controlled conditions of a new strain of Streptomyces calvus TM-521 which has been identified by the generally known ISP (International Streptomyces Project) method described by Gottlieb and Shirling.

The microbiological properties of the new strain, Streptomyces calvus TM-521 are as follows:

1. General morphological findings

The mycelium on sucrose-nitrate agar is formed with the display of slightly curved hyphae, although development of aerial mycelium is poor.

The aerial mycelia on oat-meal agar, yeast extract-malt extract agar and glucose-asparagine agar from abundant spores.

Microscopic examination of the culture grown on oat-meal agar reveals abundant aerial mycelia and spore chains with primitive spirals. A mature spore chain contains about 10 spores on the average. An electron micrograph of the spore shows an oval to spherical spore (0.7–1.0 × 1.0–1.4μ) with a hairy surface.

2. Cultural characteristics

Some cultural characteristics of Streptomyces calvus TM-521 are listed in Table 1.

Table 1.

| Cultural characteristics of Streptomyces calvus TM-521 | | | |
|---|---|---|---|
| Medium | Growth | Aerial mycelium | Soluble pigment |
| Sucrose-nitrate agar (27° C.) | poor, white to yellowish white | poor, partly white | none |
| Glucose-nitrate agar (27° C.) | weak, small colony of yellowish white | none | none |
| Glycerol-nitrate agar (27° C.) | yellowish white to yellowish brown, partly yellowish brown | white to milk white | none |
| Starch-nitrate agar (27° C.) | yellowish white to yellow | powdery, white | pale yellow |
| Glucose-asparagine agar (27° C.) | good, grayish white to yellowish white, later becoming yellowish brown | white to grayish white partly white or gray | |
| Glycerol-asparagine agar (27° C.) | good, grayish white to yellowish white | white | none |
| Salt-starch agar (27° C.) | good, yellowish white to yellowish brown | grayish white to milk white, later becoming brownish white | none |
| Nutrient agar (27° C.) | poor, yellowish white | none | none |
| Yeast extract-malt extract agar (27° C.) | good, yellowish white to yellowish brown | white to grayish white | none |
| Oat-meal agar (27° C.) | good, grayish white to grayish yellow, later becoming yellowish brown | white to grayish white | none |
| Tyrosine agar (27° C.) | good, yellowish white to yellowish brown later becoming brown | white to milk white, later becoming grayish white | pale milk yellow |
| Blood agar (37° C.) | poor, moist gray | none | none |
| Skim milk (37° C.) | weak, white | none | none |
| Gelatin | weak, | none | none |

Table 1.-continued

Cultural characteristics of *Streptomyces calvus* TM-521

| Medium | Growth | Aerial mycelium | Soluble pigment |
|---|---|---|---|
| bouillon (27° C.) | yellowish white | | |

3. Physiological properties

Physiological properties of this strain are as follows:
Growth temperature range: 20°–45° C. on oat-meal agar.
Optimum growth temperature: 30° C.
Oxygen requirement: no growth occurs under anaerobic condition.
Hydrolysis of starch: positive.
Cellulose decomposition: negative.
Coagulation of skim milk: slightly positive.
Peptonization of skim milk: negative.
Liquefaction of gelatin: slightly positive.
Liquefaction of Loeffler's coagulated serum: negative.
Blood haemolysis: positive.
Tyrosinase reaction: negative.
Melanine production: negative.
Production of hydrogen sulfide: negative.
Reduction of nitrate: negative.

The carbon source utilization test by the Pridham and Gottlieb method shows that this strain fairly to fully utilizes D-glucose, D-xylose, L-arabinose, starch, lactose, D-fructose, D-mannitol, sucrose and raffinose but does not utilize inositol, L-rhamnose, mannose, galactose and cellulose.

From the above results, the microbiological characteristics of TM-521 strain may be summarized as follows:

The strain TM-521 forms aerial mycelium with primitive spirals, and the surface of spore is hairy.

Growth on various synthetic media is generally white to yellowish white, and the mycelium is generally white to grayish white. Soluble pigment is not usually observed except for the culture on starch-nitrate agar in which pale yellow pigment develops. Vegetative mycelium on organic media shows good growth with yellowish white to yellowish brown, and the aerial mycelium colored white to grayish white is abundant.

Soluble pigment is not produced on most organic media except on tyrosine agar.

These characteristics of the strain TM-521 closely parallel those of the "the gray color" series of ISP-classified Streptomyces. Among the known species of this series, *Streptomyces calvus* (Antibiotics and Chemotherapy 7, 532–540 (1957)) is most similar to the strain TM-521 with respect to many characteristics including the form of spore-bearing hyphae and the surface of spore. This strain, however, differs from *Streptomyces calvus* in terms of its slight production of peptone from skim milk, its strong utilization of inositol and L-rhamnose, and its slight utilization of L-arabinose.

The strain, from these features, may reasonably be concluded to belong to the varietas of *Streptomyces calvus*, and it was finally designated as *Streptomyces calvus* TM-521.

This strain has been deposited in Fermentation Research Institute, Agency of Industrial Science and Industry, Japan, being registered as FERM-P No. 4283, and in the American Type Culture Collection, Rockville, Md., as ATCC No. 31,478.

The amylase inhibitors TAI-A and TAI-B can be obtained by inoculating a seed of the strain of *Streptomyces calvus* TM-521 into an aqueous nutrient medium, cultivating this with shaking or by a submerged culture method with aeration, and separating the produced amylase inhibitors TAI-A and TAI-B from the cultured broth.

As the source of assimilable carbon, various carbohydrates such as soluble starch, corn starch, potato starch, amylopectin and oat-meal are preferably used. Available sources of assimilable nitrogen include a wide variety of substances such as peptone, amino acids, casein, fish meal, soya-bean meal, meat extract, yeast extract and various other nitrogenous substances of vegetable and animal origins. Chemicals such as urea, nitrates and ammonium compounds may also be added to the nutrient media as a nitrogen source. In some cases, essential mineral salts, e.g., sodium chloride, and anti-foaming agents, e.g., silicone oil may be added to the nutrient media. The nutrient medium may contain 1–10%, preferably 2–5%, of carbon source, 0.1–4%, preferably 0.5–2%, of nitrogen source and 0.1–1% of minerals by weight.

Before sterilization, the pH value of the medium is adjusted to a pH of 5.5–8.0, preferably 6.6–7.0. Cultivation is carried out at a temperature of 20°–40° C. for 2–5 days, preferably at a temperature of 27°–35° C. for about 3 days. The development of the culture is comparatively rapid under a suitable aerated and submerged condition, and the active substances are detected in the cultured broth after 12 hours. Maximum production of both TAI-A and TAI-B is usually attained after 60–72 hours in jar fermentation. Active substances, TAI-A and TAI-B can be separated from the cultured broth easily as in the following:

After cultivation, the broth is collected by centrifugation to remove the mycelia. Active carbon is added to the broth in a concentration of 1% for the adsorption of the active substances. After being agitated for one hour, the mixture is filtered and the carbon fraction is treated with an aqueous organic solvent such as acetone, methanol or ethanol to elute the mixture of TAI-A and TAI-B. The aqueous organic solution is concentrated in vacuo. The resulting solution may be applied to the efficient combination of column chromatography using an ion exchange resin such as Amberlite IR-120(H-form), Amberlite IR-45(OH-form) and SP Sephadex C-25(H-form) silicagel column chromatography, cellulose column chromatography and gel filtration on Sephadex G-15 to give TAI-A and TAI-B respectively. One of the preferred embodiments of the isolation procedure is as follows: the aqueous solution is applied to a column of Amberlite IR-120(H-form). The column is washed with water and then eluted with 0.1 N aqueous hydrochloric acid solution. The eluate is neutralized with 2 N aqueous sodium hydroxide solution and desalted by a column chromatography on active carbon. The preparation is purified by an additional column chromatography on SP Sephadex C-25(H-form). TAI-A and TAI-B are separated from the crude solution by elution with 0.02 N aqeuous hydrochloric acid solution. TAI-A and TAI-B are eluted in the fractions between about 3.5 and 4.5 times, and between 5 and 6 times the volume of the column, respectively. The eluate is passed over a column of Amberlite IR-45(H-form). The purified TAI-A and TAI-B are obtained as white powders by lyophilization.

TAI-A and TAI-B have following physicochemical and bilogical properties.

(a) Elemental Analysis
TAI-A; C: 41.44%, H: 6.27% N: 1.32%.
TAI-B; C: 42.20%, H: 6.47%, N: 2.08%.

(b) Molecular Weight
The molecular weights of TAI-A and TAI-B are estimated to be 950–1050 and 650–700 respectively by a gel chromatography on Sephadex G-15 equilibrated with M/20 phosphate buffer containing 0.1 M potassium chloride, pH 6.8.

Maltooligosaccharides ($G_2$–$G_{10}$) are used as standards.

(c) Specific Optical Rotation
TAI-A; $[\alpha]_D^{23}$ +157.3° (c=0.5%, water).
TAI-B; $[\alpha]_D^{20}$ +142° (c=0.5%, water).

(d) Infrared Absorption Spectrum
The infrared absorption spectrum of TAI-A determined using a tablet of KBr shows characteristic bands at 3360, 2900, 1635, 1410, 1365, 1230, 1150, 1075, 1020, 925, 850, 760, 700, 570 and 520 cm$^{-1}$ (FIG. 1).

The infrared absorption spectrum of TAI-B determined using a tablet of KBr shows characteristic bands at 3360, 2920, 1630, 1410, 1365, 1250, 1150, 1075, 1020, 925, 890, 850, 750, 700, 570 and 515 cm$^{-1}$ (FIG. 2).

Figure 4:
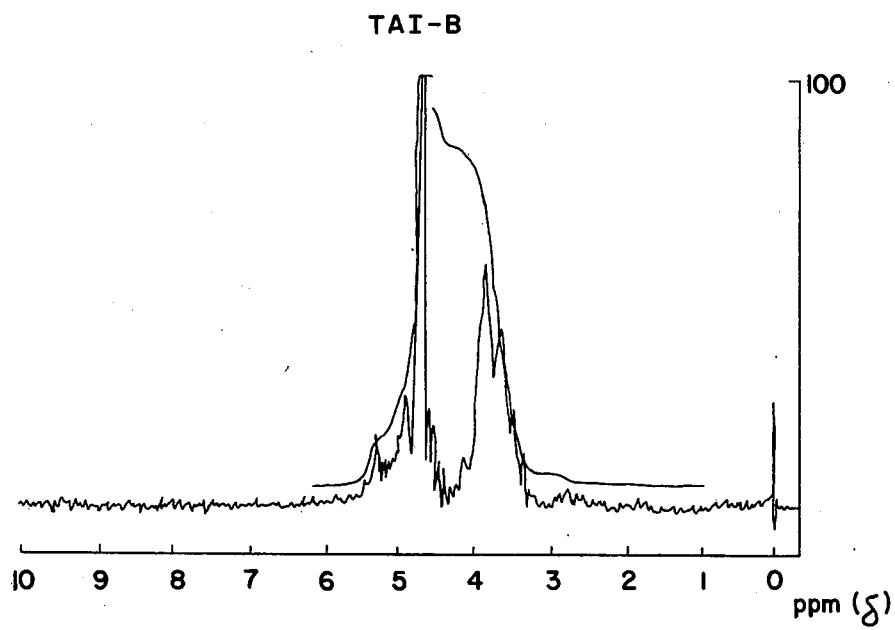
FIG. 4 shows the nuclear magnetic resonance spectrum of TAI-B in $D_2O$.

(e) Nuclear Magnetic Resonance Specturm
The nuclear magnetic resonance spectrums of TAI-A and TAI-B at 60 MHz in deutrium oxide are shown in FIGS. 3 and 4, respectively.

(f) Solubility
TAI-A is soluble in water and dimethylsulfoxide, and insoluble in methanol, ethanol, ethylacetate, chloroform, acetone and pyridine.

TAI-B is soluble in water and dimethylsulfoxide, slightly soluble in methanol and pyridine, but insoluble in ethanol, ethylacetate, chloroform and acetone.

(g) Color Reaction
Both of TAI-A and TAI-B show positive reactions in the Molisch and anthrone tests, and their acid hydrolyzates react positively with ninhydrin.

(h) pKa
TAI-A; 4.2(in water), basic.
TAI-B; 4.5(in water), basic.

(i) Appearance
Both of TAI-A and TAI-B are white powders.

(j) Rf Value
Rf values of TAI-A and TAI-B on thin layer chromatography [Silica gel 60F254 (Merk)] and paper chromatography[No. 50 (Toyo Roshi Co., LTD.)] are shown in Tables 2 and 3.

Table 2

| (TAI-A) | | | |
|---|---|---|---|
| Thin layer chromatography | | Paper chromatography | |
| Solvent system | Rf value | Solvent system | Rf value |
| 65% n-propanol n-butanol: pyridine : water (6 : 4 : 2.5) | 0.40 0.21 | 65% n-propanol pyridine: n-propanol : acetic acid: water (10 : 15 : 3 : 12) | 0.16 0.42 |

Table 3

| (TAI-B) | | | |
|---|---|---|---|
| Thin layer chromatography | | Paper chromatography | |
| Solvent system | Rf value | Solvent system | Rf value |
| 65% n-propanol n-butanol: pyridine : water (6 : 4 : 2.5) | 0.46 0.32 | 65% n-propanol pyridine: n-propanol : acetic acid : water (10 : 15 : 3 : 12) | 0.28 0.53 |

(k) Ultraviolet Absorption Spectrum
A one percent aqueous solution of TAI-A or TAI-B shows no characteristic absorption in the ultraviolet region of wave length 210–360 nm.

(l) Melting Point
TAI-A shows no clear melting point, being decomposed at 137°–142° C.
TAI-B shows no clear melting point, being decomposed at 169°–174° C.

(m) Components
TAI-A and TAI-B contain two or more glucose units and a basic substance which seems to be an amino sugar.

(n) Amylase Inhibitory Activity
Table 4 shows the degree of the inhibitory activity of TAI-A and TAI-B to various amylases.

In this table, the amylase inhibitory activity to glucoamylase, bacterial saccharifying α-amylase and β-amylase are determined by the following method:

A mixture of 50 μl of the testing amylase solution in M/20 acetate buffer (pH 5.0) and 50 μl of water is preincubated at 40° C. for 10 minutes, and then added to 400 μl of 1% soluble starch solution in M/20 acetate buffer (pH 5.0). After incubation at 40° C. for 10 minutes, 100 μl of the reaction mixture is withdrawn for the determination of the released reducing sugar according to the Somogyi-Nelson method. One unit of amylase activity is the amount of enzyme necessary to release 0.1 mg of glucose per minute in the reaction mixture at 40° C.

Further, the above-mentioned procedure is repeated except that 50 μl of an aqueous inhibitor solution is used for 50 μl of water. One unit of amylase inhibitory activity (IU) is defined as the amount of the inhibitor required to inhibit, by 50%, two units of amylase activity under the above conditions.

The percentage of the inhibitory activity is measured by the following expression $(A - B/A) \times 100$ wherein A is the amylase activity unit of the reaction mixture in the absence of the inhibitor, and B is the amylase activity unit of the reaction mixture in the presence of the inhibitor.

Further, the amylase inhibitory activity to human salivary α-amylase and hog pancreatic α-amylase are determined by the above-mentioned method except that 1% soluble starch solution in M/15 phosphate buffer containing 0.1 M sodium chloride (pH 7.0) is used instead of the 1% soluble starch solution in M/20 acetate buffer, the inhibitory activity to bacterial liquefying α-amylase and Taka-amylase are determined by dextrinizing activity according to the Wohlgmuth method modified by Tsujisaka, and the inhibitory activity to pullulanase is determined by the Kobayashi method. The activity in this table is determined at the concentration of 2 μg/ml of TAI-A and 10 μg/ml of TAI-B in the reaction mixture, respectively.

Table 4

| Amylase | intensity TAI-A | TAI-B |
|---|---|---|
| Bacterial liquefying α-amylase | − | − |
| Bacterial saccharifying α-amylase | + | + |
| Taka-amylase | + | − |
| Human salivary α-amylase | + | + |
| Hog pancreatic α-amylase | + | + |
| Glucoamylase (*Rhizopus niveus*) | + | + |
| β-amylase (soy bean) | − | − |
| Pullulanase (*Aerobacter aerogenes*) | − | − |

− 0-50% of the amylase inhibitory activity
+ more than 50% of the amylase inhibitory activity (o) Effect on Starch Hydrolysis of Glucoamylase Inhibition of TAI-A and TAI-B is of a non-competitive type.

(p) Stability

Figure 5:
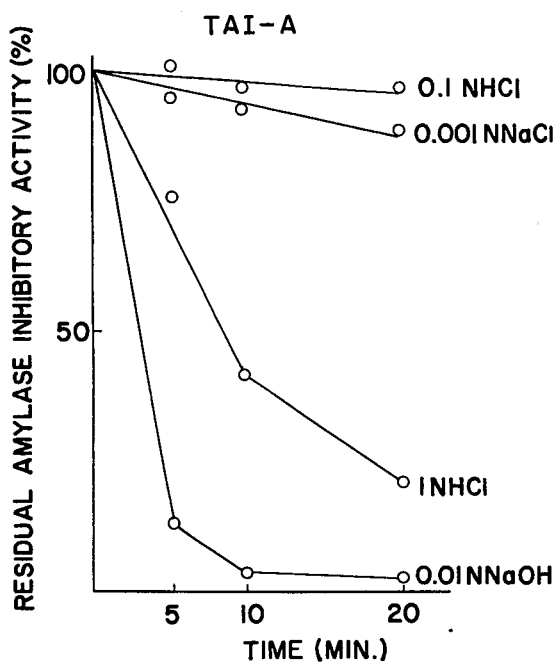
FIG. 5 shows the stability of TAI-A.
Figure 6:
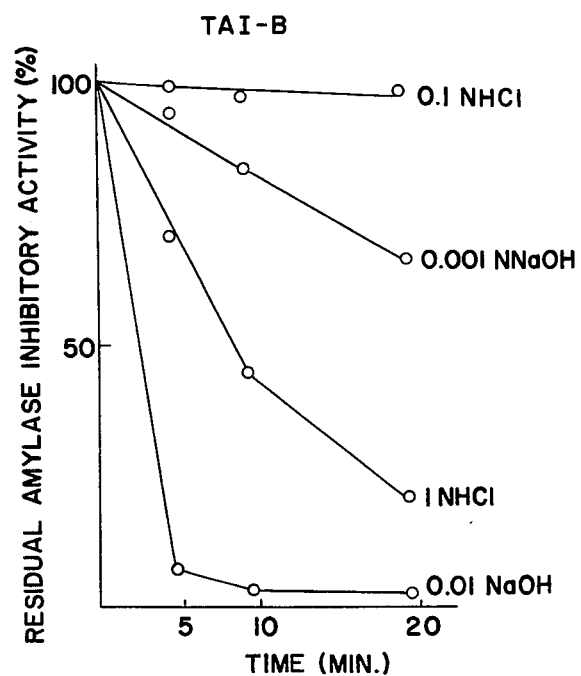
FIG. 6 shows the stability of TAI-B.

The stability of TAI-A and TAI-B in an aqueous hydrochloric acid solution and an aqueous sodium hydroxide solution is determined at 100° C. as the residual activity (%) of the glucoamylase inhibitory activity, and in the results are shown in FIGS. 5 and 6. As shown in these figures, TAI-A and TAI-B are stable and their inhibitory activity is maintained even by heating at 100° C. for 20 minutes in 0.1 N aqueous hydrochloric acid solution or 0.001 N aqueous sodium hydroxide solution.

(g) Toxicity

The toxicity of TAI-A and TAI-B is extremely low. That is, they hardly show any intravenous acute toxicity on mice when administered in a dosage less than 1 g/kg of body weight. Moreover, no side effect is observed after administration of 1 g/kg/day orally for 21 days for laboratory animals.

(r) Amylase Inhibition in Mice

Experimental techniques for demonstrating the action of the inhibitors of this inventions on mice are as follows: To produce alimentary hyperglycemia, groups of 6 ddY mice (20-22 g) are forced to fast for 24 hours, and then given orally 1 g/kg of a boiled corn starch as a suspension or 2.5 g/kg of sucrose as a solution. The other groups of 6 ddY mice (20-22 g) are given orally the same carbohydrates in the same amount and an inhibitor (200 IU/mg) of this invention in the amount indicated. The blood glucose level is determined at short intervals after administration by using Auto-Analyzer(Hitachi 500 type).

Tables 6 and 7 show the effect of TAI-A and TAI-B, respectively, on the blood glucose level of the fasting mice administered the starch. Generally, in the controls and the mice administered with the inhibitor, a temporary hyperglycemia occurs at first, the blood glucose level goes downwards and gradually ends after an hour or so. The hyperglycemia in the mice administered with the inhibitor (200 or 1000 IU) of this invention weakens quicker than that in controls.

Tables 8 and 9 show the effect of TAI-A and TAI-B, respectively on the blood glucose level of the fasting mice administered sucrose. After a temporary hyperglycemia is ended, after 15 minutes, the blood glucose level gradually recovers, and falls to the initial value after 2 or 3 hours. The administration of the inhibitor (80 or 2000 IU) of this invention weakens the intensity of the hyperglycemia.

Table 6

| Time after the administration of starch | Blood glucose (mean value ± SD) mg/100 ml TAI-A (mg/mouse) | | | |
|---|---|---|---|---|
| | 0 | 0.2 | 1.0 | 5.0 |
| 5(min.) | 234 ± 28 | 190 ± 31 | 169 ± 14 | 136 ± 23 |
| 15 | 220 ± 16 | 189 ± 17 | 143 ± 8.2 | 132 ± 4.6 |
| 30 | 183 ± 6.8 | 167 ± 21 | 139 ± 19 | 130 ± 11 |
| 60 | 160 ± 21 | 135 ± 16 | 123 ± 17 | 130 ± 5.7 |

Control level: 132 ± 16 mg/100 ml

Table 7

| Time after the administration of starch | Blood glucose (mean value ± SD) mg/100 ml TAI-B (mg/mouse) | | | |
|---|---|---|---|---|
| | 0 | 0.2 | 1.0 | 5.0 |
| 5(min.) | 248 ± 27 | 202 ± 9.1 | 158 ± 13 | 136 ± 29 |
| 15 | 218 ± 31 | 178 ± 22 | 138 ± 8.5 | 128 ± 19 |
| 30 | 178 ± 8.6 | 158 ± 10 | 134 ± 21 | 130 ± 11 |
| 60 | 162 ± 13 | 130 ± 16 | 132 ± 14 | 128 ± 7.2 |

Control level: 130 ± 8.2 mg/100 ml

Table 8

| Time after the administration of sucrose | Blood glucose (mean value ± SD) mg/100 ml TAI-A (mg/mouse) | | | |
|---|---|---|---|---|
| | 0 | 0.4 | 2.0 | 10.0 |
| 0(min.) | 102 ± 9.2 | 93 ± 10 | 98 ± 5.9 | 119 ± 9.5 |
| 15 | 288 ± 35 | 154 ± 27 | 127 ± 10 | 140 ± 11 |
| 30 | 217 ± 30 | 193 ± 25 | 185 ± 41 | 142 ± 14 |
| 60 | 198 ± 23 | 168 ± 18 | 113 ± 10 | 109 ± 12 |
| 120 | 151 ± 19 | 142 ± 11 | 140 ± 15 | 134 ± 5.4 |
| 180 | 156 ± 12 | 159 ± 9.8 | 131 ± 5.2 | 127 ± 10 |

Control level: 122 ± 18 mg/100 ml

Table 9

| Time after the administration of source | Blood glucose (mean value ± SD) mg/100 ml TAI-B (mg/mouse) | | | |
|---|---|---|---|---|
| | 0 | 0.4 | 2.0 | 10.0 |
| 0(min.) | 98 ± 8.9 | 89 ± 5.3 | 92 ± 6.4 | 94 ± 7.2 |
| 15 | 276 ± 22 | 142 ± 8.5 | 123 ± 9.8 | 118 ± 12 |
| 30 | 208 ± 19 | 194 ± 23 | 172 ± 11 | 140 ± 17 |
| 60 | 188 ± 17 | 172 ± 18 | 123 ± 22 | 108 ± 10 |
| 120 | 162 ± 23 | 136 ± 12 | 134 ± 12 | 128 ± 7.3 |
| 180 | 148 ± 19 | 152 ± 35 | 142 ± 35 | 134 ± 19 |

Control level: 126 ± 21 mg/100 ml

From these properties, it is apparent that both TAI-A and TAI-B belong to the group of oligosaccharide amylase inhibitors, and that they differ from the known amylase inhibitors. Namely, they differ from Nojirimycin because it has a molecular weight of 179 and has inhibitory activity to β-glucosidase. S-AI differs from TAI-A and TAI-B in its strong inhibitory activity to bacterial liquefying α-amylase and in its non-adsorptive nature toward acidic and basic ion exchange resins. TAI-A and TAI-B are similar to NCGAI in that both are oligosaccharides containing glucose and are adsorbed by strong acidic ion exchange resins. However, TAI-A differs from NCGAI in its molecular weight, decomposition point, optical activity and some biological properties. Namely, NCGAI is of molecular weight 600, is decomposed at 270°-300° C., has no optical activity and shows only a slight inhibitory activity to human salivary α-amylase and bacterial liquefying α-amylase. On the other hand, TAI-A is of molecular weight about 1000, is decomposed at 137°-142° C., and strongly inhibits human salivary α-amylase, bacterial saccharifying α-amylase and hog pancreatic α-amylase as well as glucoamylase, but does not inhibit bacterial liquefying α-amylase. Though TAI-B shows almost the same molecular weight as NCGAI, it differs from NCGAI in decomposition point, optical activity and some biological properties. That is, TAI-B is decomposed at 169°–174° C. and shows an optical activity but does not inhibit bacterial liquefying α-amylase.

The aminosugar derivative amylase inhibitors by Frommer et al consist of 4,6-bisdeoxy-4-(1S-(1,4,6/5)-4,5,6-trihydroxy-3-hydroxymethylcyclohex-2-en-1-yl-amino)-α-D-glucopyranose and one or more glucose units. TAI-A and TAI-B do not have any methyl group in their molecules, judging from their NMR spectra. Therefore, they differ from the aminosugar derivatives by Frommer et al.

TAI-A and TAI-B differ each other in molecular weight and in the degree of the inhibitory activity to human salivary α-amylase, Taka-amylase, and hog pancreatic α-amylase.

The amylase inhibitors of this invention are suitable for use as therapeutic agents for the following indications in mammals: obesity, adiposit, hyperlipidemia (arteriosclerosis), diabetes, pre-diabetes, agastitis, gastric ulcer, duodenal ulcer, and caries.

The pharmaceutical forms contemplated by this invention include pharmaceutical compositions suited for oral, and parenteral use, e.g., tablets, powder packets, cachets, dragees, capsules, solutions, suspensions, sterile injectable forms, suppositories, bougies, and like.

Optional diluents to be used in pharmaceutical compositions adapted to be formed into tablets, dragees, capsules and pills include the following: fillers and extenders, e.g., starch, sugar, mannitol, and silicic acid; binding agents, e.g., carboxymethyl cellulose and other cellulose derivatives, alginates, gelatin, and polyvinyl pyrrolidone; moisturizing agents, e.g., glycerol; disintegrating agents, e.g., agar-agar, calcium carbonate, and sodium bicarbonate; agents for regarding dissolution, e.g., paraffin; resorption accelerators, e.g., quaternary ammonium compounds; surface active agents, e.g., cetyl alcohol, glycerol monostearate; adsorptive carriers, e.g., kaolin and bentonite; lubricants, e.g., talc, calcium and magnesium stearate, and solid polyethylene glycols; elastomeric binders such as chicle.

The pharmaceutical compositions preferably contain about 0.1 to 99.5, more preferably from about 0.5 to 95.5 percent of the inhibitor by weight of the total composition. In addition to an inhibitor of the invention, the pharamceutical compositions according to the invention can also contain other pharmaceutically active compounds. They may also contain a plurality of different inhibitors of the invention. Particular examples of such other pharmaceutically active compounds are oral anti-diabetic agents such as β-cytotropic sulphonyl-urea derivatives and biguanides which influence the blood sugar level.

The preferred unit dose for the medicaments of this invention is 10 mg–500 mg, preferably 20 mg–100 mg of the inhibitor. The unit dose may be administered to mammals orally once of several times daily, usually immediately before, during, or after meal.

The following example illustrates the production of the inhibitors of this invention.

EXAMPLE

Streptomyces TM-521 preserved on an oat-meal agar slant is inoculated for a seed-culture into 500 milliliters of an autoclaved nutrient solution containing 2% oat-meal (pH 6.8) in a 2 liter Sakaguchi flask. The seed-culture is carried out at 30° C. for 48 hours with shaking. Five hundred milliliters of the seed is transferred into a 30 liter fermenter containing 20 liters of the same aqueous medium sterilized at 121° C. for 30 minutes. The culture in the fermenter is carried out at 30° C. for 65 hours with aeration and agitation. The cultured broth is centrifuged to remove mycelia. Fifteen liters of supernatant liquor containing about 200,000 IU/l of the inhibitory activity to glucoamylase are obtained. To the supernatant is added active carbon at the concentration of 1% (W/V). TAI-A and TAI-B are adsorbed on active carbon, followed by a filtration separation into filtrate and active carbon sediment. The latter is washed with 6 liters of water and eluted with 4 liters of 50% aqueous acetone. The active fraction is concentrated to about 1000 milliliters in vacuo. This concentrate has $1.5 \times 10^5$ IU/ml. For further purification, the concentrate is applied to an Amberlite IR-120 column (H-form, 4×73 cm). The column is washed with 3 liters of water and eluted with 0.1 N aqueous hydrochloric acid solution. The active fraction is neutralized with 2 N aqueous sodium hydroxide solution and desalted by a column chromatography on active carbon. Then, the active fraction is concentrated to about 1000 mililiters in vacuo. The inhibitor solution is applied to SP Sephadex C-25 (H-form, 4×73 cm) column. The amylase inhibitors, TAI-A and TAI-B, are adsorbed. The column is washed with 3 liters of water and eluted with 0.02 N aqueous hydrochloric acid solution. TAI-A and TAI-B are eluted in the fractions between about 3.5 and 4.5 times, and between 5 and 6 times the volume of the column, respectively. Thus, the elution chromatograms of TAI-A and TAI-B from SP Sephadex C-25 column differ from each other. The active fraction of TAI-A and that of TAI-B are respectively passed over an Amberlite IR-45 column (OH-form). Each active eluate is concentrated to 20 mililiters in a rotary evaporator and lyophilized. Yield: 400 mg of TAI-A as white powder of 1300 IU/mg; 300 mg of TAI-B as white powder of 1900 IU/mg.

What we claim is:

1. An amylase inhibitor, TAI-A; being a white amorphous powder; having a decomposition point at 137°–142° C.; containing carbon, hydrogen and nitrogen with the analytical values (%) of C: 41.44, H: 6.27, N: 1.32; having an optical rotatory value of $[\alpha]_D^{23} = +157.3°$ (c=0.5%, water); having a pKa value of 4.2 (in water); being of molecular weight 950–1050 as determined by gel filtration; being soluble in water and dimethylsulfoxide, and insoluble in methanol, pyridine, ethanol, ethylacetate, chloroform and acetone; having the infrared absorption spectrum shown in FIG. 1; having the nuclear magnetic resonance spectrum shown in FIG. 3; giving positive reactions with Molisch and anthrone; its acid hydrolyzate giving a positive reaction with ninhydrin; and showing the Rf values on thin layer chromatography and paper chromatography as follows:

| Thin layer chromatography | | Paper chromatography | |
|---|---|---|---|
| Solvent system | Rf value | Solvent system | Rf value |
| 65% n-propanol n-butanol:pyridine :water | 0.40 0.21 | 65% n-propanol pyridine:n-propanol :acetic acid:water | 0.16 0.42 |

| Thin layer chromatography | | Paper chromatography | |
|---|---|---|---|
| Solvent system | Rf value | Solvent system | Rf value |
| (6:4:2.5) | | (10:15:3:12) | |

2. An amylase inhibitor, TAI-B; being a white amorphous powder; having a decomposition point at 169°–174° C.; containing carbon, hydrogen and nitrogen with the analytical values (%) of C: 42.20, H: 6.47, N: 2.08; having an optical rotatory value of $[\alpha]_D^{20} = +142°$ (c=0.5%, water); having a pKa value of 4.5 (in water); being of molecular weight 650–700 as determined; being soluble in water and dimethylsulfoxide, slightly soluble in methanol and pyridine, and insoluble in ethanol, ethylacetate, chloroform or acetone; having the infrared absorption spectrum shown in FIG. 2; having the nuclear magnetic resonance spectrum shown in FIG. 4; giving positive reactions with Molisch and anthrone; its acid hydrolyzate giving a positive reaction with ninhydrin; and showing the Rf values on thin layer chromatography and paper chromatography as follows:

| Thin layer chromatography | | Paper chromatography | |
|---|---|---|---|
| Solvent system | Rf value | Solvent system | Rf value |
| 65% n-propanol | 0.46 | 65% n-propanol pyridine:propanol | 0.28 |
| n-butanol:pyridine:water | 0.32 | :acetic acid:water | 0.53 |
| (6:4:2.5) | | (10:15:3:12) | |

* * * * *

UNITED STATES PATENT AND TRADEMARK OFFICE
CERTIFICATE OF CORRECTION

PATENT NO. : 4,197,292
DATED : April 8, 1980
INVENTOR(S) : KUNIO KANGOURI ET AL

It is certified that error appears in the above-identified patent and that said Letters Patent are hereby corrected as shown below:

Column 1, line 33, delete "the".

Column 2, line 10, "from" should read --form--.

Column 7, line 21, "and an" should read --and in an--;

line 24, "and in the" should read --and the--.

Column 8, Table 9, under heading "10.0", fifth number in column should read --128 $\pm$ 7.8--.

IN THE CLAIMS

Claim 2, line 8, after "determined" insert --by gel filtration--.

Signed and Sealed this

Tenth Day of June 1980

[SEAL]

Attest:

SIDNEY A. DIAMOND

*Attesting Officer*  *Commissioner of Patents and Trademarks*